United States Patent
Markosyan et al.

(10) Patent No.: US 12,193,460 B2
(45) Date of Patent: Jan. 14, 2025

(54) HIGHLY SOLUBLE STEVIOL GLYCOSIDES

(71) Applicant: PureCircle USA Inc., Oak Brook, IL (US)

(72) Inventors: Avetik Markosyan, Yerevan (AM); Saravanan Ramandach, Seremban (MY); Kian Pin Tan, Batu Pahat (MY); Mohamad Afzaal Bin Hasim, Kuala Lumpur (MY)

(73) Assignee: PureCircle Usa Inc., Oak Brook, IL (US)

( * ) Notice: Subject to any disclaimer, the term of this patent is extended or adjusted under 35 U.S.C. 154(b) by 0 days.

(21) Appl. No.: 16/068,244

(22) PCT Filed: Jan. 6, 2017

(86) PCT No.: PCT/US2017/012548
§ 371 (c)(1),
(2) Date: Jul. 5, 2018

(87) PCT Pub. No.: WO2017/120480
PCT Pub. Date: Jul. 13, 2017

(65) Prior Publication Data
US 2019/0014805 A1 Jan. 17, 2019

Related U.S. Application Data

(60) Provisional application No. 62/275,887, filed on Jan. 7, 2016.

(51) Int. Cl.
| | | |
|---|---|---|
| *A23L 27/30* | (2016.01) | |
| *A23L 5/00* | (2016.01) | |
| *A23L 5/30* | (2016.01) | |
| *A23P 10/40* | (2016.01) | |
| *C07H 1/00* | (2006.01) | |
| *C07H 15/24* | (2006.01) | |

(52) U.S. Cl.
CPC ............... *A23L 27/36* (2016.08); *A23L 5/30* (2016.08); *A23L 5/51* (2016.08); *A23L 27/30* (2016.08); *A23P 10/40* (2016.08); *C07H 1/00* (2013.01); *C07H 15/24* (2013.01); *A23V 2002/00* (2013.01); *A23V 2200/238* (2013.01); *A23V 2250/258* (2013.01); *A23V 2250/262* (2013.01); *A23V 2300/20* (2013.01); *A23V 2300/24* (2013.01); *A23V 2300/31* (2013.01)

(58) Field of Classification Search
CPC . A23L 27/30; A23L 27/36; A23L 5/30; A23L 5/51
See application file for complete search history.

(56) References Cited

U.S. PATENT DOCUMENTS

| | | | |
|---|---|---|---|
| 7,923,541 B2 | 4/2011 | Yang et al. | |
| 8,030,481 B2 | 10/2011 | Prakash et al. | |
| 8,299,224 B2 | 10/2012 | Abelyan et al. | |
| 8,703,224 B2 | 4/2014 | Lee | |
| 8,981,081 B2 | 3/2015 | Markosyan | |
| 9,029,426 B2 | 5/2015 | Markosyan et al. | |
| 9,060,537 B2 | 6/2015 | Mutilangi et al. | |
| 9,243,273 B2 | 1/2016 | Markosyan et al. | |
| 9,427,006 B2 | 8/2016 | Markosyan | |
| 9,752,174 B2 | 8/2017 | Markosyan et al. | |
| 10,004,245 B2 | 6/2018 | Purkayastha et al. | |
| 10,264,811 B2 | 4/2019 | Shi et al. | |
| 10,611,789 B2 | 4/2020 | Zhu et al. | |
| 10,905,146 B2 | 2/2021 | Prakash et al. | |
| 2008/0300402 A1* | 12/2008 | Yang | A23L 33/105 536/128 |
| 2011/0038957 A1 | 2/2011 | Fowler et al. | |
| 2011/0092684 A1* | 4/2011 | Abelyan | C07H 15/24 536/18.1 |
| 2011/0195161 A1† | 8/2011 | Upreti | |
| 2012/0282389 A1* | 11/2012 | Purkayastha | A23C 9/1307 426/658 |
| 2013/0071339 A1* | 3/2013 | Markosyan | A61K 31/7034 424/49 |
| 2013/0274351 A1* | 10/2013 | Markosyan | A23L 2/60 514/777 |
| 2014/0171519 A1† | 6/2014 | Praksh | |
| 2014/0357588 A1* | 12/2014 | Markosyan | A24B 15/10 514/34 |
| 2015/0017284 A1† | 1/2015 | Praksh | |
| 2015/0031869 A1* | 1/2015 | Markosyan | C07H 15/24 536/18.1 |

FOREIGN PATENT DOCUMENTS

| | | |
|---|---|---|
| CN | 101095500 A | 1/2008 |
| CN | 101765605 A | 6/2010 |
| CN | 105037458 A | 11/2015 |
| DE | 2351385 A1 | 4/1975 |

(Continued)

OTHER PUBLICATIONS

Upreti et al., "Solubility Enhancement of Steviol Glycosides and Characterization of Their Inclusion Complexes with Gamma-Cyclodextrin", International Journal of Molecular Sciences, (2011) vol. 12, No. 12, pp. 7529-7553.

(Continued)

*Primary Examiner* — Stephanie A Cox

(57) ABSTRACT

A method for making a highly soluble steviol glycoside composition is described. The resulting composition readily provides solutions with at least 0.5% concentration.

8 Claims, No Drawings

(56) References Cited

FOREIGN PATENT DOCUMENTS

| | | |
|---|---|---|
| WO | 2010117346 A2 | 10/2010 |
| WO | WO2010118218 A1 | 10/2010 |
| WO | WO2011059954 A1 | 5/2011 |
| WO | 2012082587 A2 | 6/2012 |
| WO | 2013036366 A1 | 3/2013 |

OTHER PUBLICATIONS

Nguyen, et al. "Enhancement of quercetin water solubility with steviol glucosides and the studies of biological properties". Functional Foods in Health and Disease. (2015) pp. 437-449.

\* cited by examiner
† cited by third party

HIGHLY SOLUBLE STEVIOL GLYCOSIDES

FIELD OF THE INVENTION

The invention relates to a process for the preparation of highly soluble individual or combined steviol glycosides, and more particularly for preparation of highly soluble rebaudioside M.

DESCRIPTION OF THE RELATED ART

It is well known that steviol glycosides exhibit so called polymorphism (Zell et al., 2000). It was described that Rebaudioside A amorphous, anhydrous and solvate forms differ significantly from each other in terms of solubility which is one of the main criteria for the commercial viability of a sweetener. In this regard, as shown in Table 1, the hydrate form of Rebaudioside A displays the lowest solubility (Prakash et al., 2008). It was shown that Rebaudioside A may transform from one polymorph form to another at certain conditions (U.S. patent application Ser. No. 11/556,049).

TABLE 1

Properties of Rebaudioside A forms (US Pat. Appl. 11/556,049)

| | Polymorph Forms | | | |
|---|---|---|---|---|
| | Form 1 Hydrate | Form 2 Anhydrous | Form 3 Solvate | Form 4 Amorphous |
| Rate of dissolution in $H_2O$ at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 1-3% | <0.05% |
| Moisture content | >5% | <1% | <3% | 6.74% |

Patent application WO/2010/118218 describes a process of producing highly soluble rebaudioside A by preparing a highly soluble hydrated crystalline form. However the described methodology utilizes low throughput techniques such as evaporative crystallization or hot filtration/centrifugation of slurries which can be hard to accomplish in large industrial scale.

It is known (Prakash et al., 2008) that rebaudioside A amorphous forms prepared by spray drying display high solubility. On the other hand extended exposure of rebaudioside A and other steviol glycosides to high temperatures results in hydrolytic decomposition of the material (Prakash et al., 2008).

Recently, rebaudioside M (also called rebaudioside X), was isolated from *Stevia rebaudiana* and characterized. Rebaudioside M and Rebaudioside D are known to have superior taste characteristics compared to other known steviol glycosides. However these 2 compounds also have very low water solubility.

A concentration of at least 0.3% (% w/w) is useful in syrup and beverage formulations. However, crystalline rebaudioside M has poor aqueous solubility and dissolution qualities in beverage formulations.

Pure (>95% w/w) Rebaudioside M has about 0.1% water solubility at room temperature. Rebaudioside D has less than 0.05% water solubility at room temperature (25° C.). Thus, there remains a need for compositions containing rebaudioside M that have improved aqueous solubility. In particular, there is a need for compositions containing rebaudioside M that have improved aqueous solubility over extended periods of time and methods for preparing such compositions.

It is also known that steviol glycosides used as food additives are required to have at least 95% (w/w) total steviol glycosides (TSG) content.

Therefore a high throughput process of manufacturing highly soluble Rebaudioside M or other steviol glycosides in industrial scale without risk of thermal degradation of the material will offer certain advantages compared to other techniques known to art.

SUMMARY OF THE INVENTION

The invention is directed to a method for producing a sweetener comprising the steps of providing a *Stevia* sweetener powder, solubilizing it in the by applying heat, cooling the obtained *Stevia* sweeten solution to produce solidified (frozen) solution, and freeze drying the frozen solution to obtain a highly soluble *Stevia* sweetener powder.

Hereinafter the term "steviol glycoside(s)" will mean Rebaudioside A, Rebaudioside B, Rebaudioside C, Rebaudioside D, Rebaudioside E, Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Stevioside, Steviolbioside, Dulcoside A, Rubusoside, or other glycoside of steviol found in *Stevia rebaudiana* plant or synthesized by various methods and combinations thereof.

Hereinafter, unless specified otherwise, the solubility of material is determined in RO (reverse osmosis) water at room temperature (25° C.). Where the solubility is expressed as "%" it to be understood as number of grams of material soluble in 100 grams of solvent.

The material is deemed soluble at certain concentration if the produced solution has <10 FAU (Formazin Attenuation Unit) turbidity value.

It is to be understood that both the foregoing general description and the following detailed description are exemplary and explanatory and are intended to provide further explanation of the invention as claimed.

DETAILED DESCRIPTION OF THE INVENTION

A process for the preparation of highly soluble *Stevia* sweetener, particularly Rebaudioside M composition, is described herein.

Crystalline Rebaudioside M has an inherently very low solubility, ranging from about 0%-0.1%.

Typical spray drying techniques are used to increase the solubility of steviol glycosides compositions. However the heat applied in spray drying may cause thermal degradation of material a reducing its purity below legally permitted levels. Therefore there's a need to develop a new method of increasing the solubility of steviol glycosides with minimal heat exposure and heat degradation.

In one embodiment of the present invention, an initial material, comprising sweet glycoside(s) occurring in *Stevia rebaudiana* plant, which includes Rebaudioside A, Rebaudioside B, Rebaudioside C, Rebaudioside D, Rebaudioside E, Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Stevioside, Steviolbioside, Dulcoside A, Rubusoside, or other glycoside of steviol and combinations thereof was combined with the water.

The obtained mixture was further subjected to heating which resulted in steviol glycosides solution. The mixture was heated to the temperature of 50-110° C., preferably 80-100° C. and was held at maximum temperature for 0-120 sec, preferably 1-10 sec.

After the heat treatment the solution was quickly cooled down to below freezing temperature. In one embodiment the mixture was cooled to the temperature −1° C. to −200° C., preferably −24° C. to −196° C.

The frozen solution was freeze dried by laboratory freeze dried until <1% water content. A highly soluble amorphous form of rebaudioside M was obtained having 2% solubility in water at room temperature.

The process of the present invention resulted in a Rebaudioside M composition which demonstrated high degree of solubility in water. Although the foregoing embodiments describe the use of Rebaudioside M, it is to be understood that any composition comprising at least one steviol glycosides and having water solubility of 0.1% and less may be used as starting material to prepare highly soluble steviol glycosides composition having water solubility of 0.5% and more in accordance with this invention. Particularly highly soluble steviol glycosides compositions of present invention can have water solubility not less than 0.5% 0.6%, 0.7%, 0.8% 0.9%, 1.0%, 1.1%, 1.2%, 1.3%, 1.4%, 1.5%, 1.6%, 1.7%, 1.8%, 1.9%, 2%, 3%, 4%, 5%, 6%, 9%, 10%. The compositions can be used as sweetener, sweetness enhancer, flavor enhancer sweetness modifier, flavor modifier in various food and beverage products at the concentration from 0.1 ppm to 999,999 ppm. Non-limiting examples of food and beverage products include carbonated soft drinks, ready to drink beverages, energy drinks, isotonic drinks, low-calorie drinks, zero-calorie drinks, sports drinks, sodas, colas, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like, at the concentration from 0.1 ppm to 999,999 ppm.

The obtained compositions can be used "as-is" or in combination with other sweeteners, flavors and food ingredients.

Non-limiting examples of sweeteners include at least one sweetener selected from group including steviol glycosides, Rebaudioside A, Rebaudioside B, Rebaudioside C, Rebaudioside D, Rebaudioside E, Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Stevioside, Steviolbioside, Dulcoside A, Rubusoside, or other glycoside of steviol and combinations thereof, glycosylated steviol glycosides, glucosylated steviol glycosides, fructosylated steviol glycosides, galactosylated steviol glycosides, enzymatically modified steviol glycosides as well as other steviol glycosides found in Stevia rebaudiana plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include at least one flavor selected from the group including lemon, orange, fruit, banana, grape, pear, pineapple, bitter almond, cola, cinnamon, sugar, cotton candy, vanilla flavors, terpenoid glycosides and/or combinations thereof.

Non-limiting examples of other food ingredients include at least one selected from group of flavors, acidulants, organic acids, amino acids, coloring agents, bulking agents, modified starches, gums, texturizers, preservatives, antioxidants, emulsifiers, stabilisers, thickeners, caffeine, gelling agents and/or combinations thereof.

The following examples illustrate preferred embodiments of the invention. It will be understood that the invention is not limited to the materials, proportions, conditions and procedures set forth in the examples, which are only illustrative.

EXAMPLE 1

Preparation of Steviol Glycosides Concentrated Solution 5 g of rebaudioside M produced by PureCircle Sdn Bhd (Malaysia) containing Rebaudioside M 83.2%, Rebaudioside D 10.5%, Rebaudioside A 1.5%, Stevioside 0.1%, Rebaudioside B 0.95%, all percentages being on a percent dried weight basis, and having water solubility of 0.05% was mixed with 50 g of water and boiled on a laboratory heater until complete dissolution.

EXAMPLE 2

Preparation of Spray Dried Highly Soluble Steviol Glycosides

Rebaudioside M solution prepared according to EXAMPLE 1, was dried using YC-015 laboratory spray drier (Shanghai Pilotech Instrument & Equipment Co. Ltd., China) operating at 175° C. inlet and 100° C. outlet temperature to yield Sample #1.

EXAMPLE 3

Preparation of Steviol Glycosides Frozen Solution

The beaker with Rebaudioside M solution prepared according to EXAMPLE 1, was transferred directly from heater to laboratory freezer operating at −24° C. Upon complete solidification the obtained frozen solution A was placed in liquid nitrogen.

EXAMPLE 4

Preparation of Steviol Glycosides Frozen Solution

The beaker with Rebaudioside M solution prepared according to EXAMPLE 1, was transferred directly from heater into to liquid nitrogen. Upon complete solidification the obtained frozen solution B was kept in liquid nitrogen.

EXAMPLE 5

Preparation of Freeze Dried Highly Soluble Steviol Glycosides

Rebaudioside M frozen solution A and frozen solution B prepared according to EXAMPLE 3 and EXAMPLE 4 were dried using ALPHA 1-4 LSC laboratory freeze drier (Martin Christ, Germany) until <1% water content. The frozen solution A yielded Sample #2, Solution #2 and frozen solution B yielded Sample #3.

The obtained highly soluble steviol glycosides samples and initial crystalline material were compared for solubility (Table 2) and were subjected to HPLC assay for steviol glycoside content analysis (Table 3).

TABLE 2

Highly soluble steviol glycosides

| Solubility at % w/w | Initial crystalline Reb M | Turbidity (FAU) | | |
|---|---|---|---|---|
| | | Sample#1 | Sample#2 | Sample#3 |
| 0.05 | 10 | 0 | 0 | 0 |
| 0.5 | Unreadable | 9 | 7 | 0 |
| 1% | Unreadable | 14 | 13 | 4 |
| 2% | Unreadable | 21 | 16 | 9 |

TABLE 3

HPLC assay of soluble steviol glycosides

| Sample ID | HPLC Assay % w/w | | | | | |
|---|---|---|---|---|---|---|
| | RebD | RebM | RebA | Stev | RebB | TSG |
| Initial crystalline Reb M | 10.48 | 83.25 | 1.46 | 0.10 | 0.95 | 96.24 |
| Sample #1 | 10.09 | 80.37 | 1.38 | 0.10 | 1.58 | 93.52 |
| Sample #2 | 10.42 | 83.23 | 1.48 | 0.10 | 0.97 | 96.20 |
| Sample #3 | 10.43 | 83.26 | 1.45 | 0.10 | 0.95 | 96.19 |

The HPLC data suggests thermal degradation of Sample #1. Sample #2 and Sample #3 show no degradation of steviol glycosides and better solubility in water.

Although the invention and its advantages have been described in detail, it should be understood that various changes, substitutions and alterations can be made herein without departing from the spirit and scope of the invention as defined by the appended claims. Moreover, the scope of the application is not intended to be limited to the particular embodiments of the invention described in the specification. As one of ordinary skill in the art will readily appreciate from the disclosure of the invention, the compositions, processes, methods, and steps, presently existing or later to be developed that perform substantially the same function or achieve substantially the same result as the corresponding embodiments described herein may be utilized according to the invention.

We claim:

1. A method for producing a highly soluble steviol glycoside composition in amorphous form comprising the steps of:
   A) providing a powder composition comprising at least one steviol glycoside
   B) providing water;
   C) mixing the water and powder composition comprising at least one steviol glycoside to make a mixture;
   D) increasing the temperature of the mixture to make a solution;
   E) decreasing the temperature of the solution to −196° C. to obtain a frozen solution; and
   F) freeze drying the frozen solution, to provide the highly soluble steviol glycoside composition in amorphous form having a water content of less than 1.0%, wherein the steviol glycoside composition has at least 0.5% solubility in water.

2. The method of claim 1 wherein steviol glycoside is selected from a group consisting of Rebaudioside A, Rebaudioside B, Rebaudioside C, Rebaudioside D, Rebaudioside E, Rebaudioside F, Rebaudioside G, Rebaudioside H, Rebaudioside I, Rebaudioside J, Rebaudioside K, Rebaudioside L, Rebaudioside M, Rebaudioside N, Rebaudioside O, Rebaudioside Q, Stevioside, Steviolbioside, Dulcoside A, Rubusoside, or other glycoside of steviol and combinations thereof.

3. The method of claim 1 wherein the water and powder composition comprising at least one steviol glycoside ratio is 10:1 (w/w).

4. The method of claim 1 wherein the water and powder composition comprising at least one steviol glycoside is heated to 80-100° C.

5. The method of claim 1 wherein the frozen solution is dried by a freeze drying apparatus.

6. The method of claim 1, wherein the highly soluble steviol glycoside composition solubility in water is about 2 grams per 100 grams of water.

7. The method of claim 1, wherein the powder composition comprising at least one steviol glycoside has 0.1% or less solubility in water.

8. A highly soluble steviol glycoside composition powder made by the process of claim 1.

* * * * *